United States Patent [19]

Lee

[11] Patent Number: 4,561,882
[45] Date of Patent: Dec. 31, 1985

[54] 3-ALKOXY-4-SUBSTITUTED-PHENOXY-2,3-UNSATURATED ACID ESTERS AND DERIVATIVES THEREOF AND THE USE THEREOF FOR THE CONTROL OF WEEDS

[75] Inventor: Shy-Fuh Lee, Sunnyvale, Calif.

[73] Assignee: Zoecon Corporation, Palo Alto, Calif.

[21] Appl. No.: 486,750

[22] Filed: Apr. 20, 1983

Related U.S. Application Data

[60] Continuation-in-part of Ser. No. 388,333, Jun. 14, 1982, abandoned, and a continuation-in-part of Ser. No. 379,609, May 19, 1982, Pat. No. 4,529,438, which is a continuation-in-part of Ser. No. 361,161, Mar. 23, 1982, Pat. No. 4,525,205, which is a continuation-in-part of Ser. No. 341,736, Jan. 22, 1982, Pat. No. 4,429,167, which is a continuation-in-part of Ser. No. 299,413, Sep. 4, 1981, Pat. No. 4,408,076, which is a continuation-in-part of Ser. No. 270,938, Jun. 5, 1981, abandoned, which is a continuation-in-part of Ser. No. 196,795, Oct. 14, 1980, abandoned, said Ser. No. 388,333, is a division of Ser. No. 314,639, Oct. 26, 1981, abandoned, which is a continuation-in-part of Ser. No. 299,413, Ser. No. 270,938, and Ser. No. 196,795.

[51] Int. Cl.⁴ .................. A01N 43/40; C07D 213/64

[52] U.S. Cl. .......................... 71/94; 546/301; 546/302

[58] Field of Search ............... 546/301, 302; 71/94

[56] References Cited

U.S. PATENT DOCUMENTS

| | | | |
|---|---|---|---|
| 4,105,435 | 8/1978 | Nishiyama et al. | 71/94 |
| 4,133,675 | 1/1979 | Schurter et al. | 546/302 |
| 4,348,221 | 9/1982 | Szczepanski et al. | 546/302 |
| 4,429,167 | 1/1984 | Lee | 568/636 |
| 4,441,913 | 4/1984 | Aya et al. | 546/302 |
| 4,469,872 | 9/1984 | Anderson et al. | 546/302 |
| 4,483,992 | 11/1984 | Kohn et al. | 546/302 |
| 4,491,468 | 1/1985 | Johnston et al. | 546/302 |

FOREIGN PATENT DOCUMENTS

| | | | |
|---|---|---|---|
| 7900624 | 9/1979 | European Pat. Off. | 546/301 |
| 0050019 | 4/1982 | European Pat. Off. | 560/61 |

*Primary Examiner*—Ethel G. Love
*Attorney, Agent, or Firm*—Darby & Darby

[57] ABSTRACT

This invention relates to 3-alkoxy-4-substituted-phenoxy-2,3-unsaturated acid esters, derivatives thereof, and the use of said acid esters and derivatives for the control of weeds.

30 Claims, No Drawings

3-ALKOXY-4-SUBSTITUTED-PHENOXY-2,3-UNSATURATED ACID ESTERS AND DERIVATIVES THEREOF AND THE USE THEREOF FOR THE CONTROL OF WEEDS

This is a continuation-in-part of Ser. No. 379,609 filed on May 19, 1982, now U.S. Pat. No. 4,529,438, which is a continuation-in-part of Ser. No. 361,161, filed Mar. 23, 1982, now U.S. Pat. No. 4,525,205, which is in turn a continuation-in-part of Ser. No. 341,736, filed Jan. 22, 1982, now U.S. Pat. No. 4,429,167, which is a continuation-in-part of Ser. No. 299,413, filed Sept. 4, 1981, now U.S. Pat. No. 4,408,076 which is a continuation-in-part of Ser. No. 270,938, filed June 5, 1981 (now abandoned) which is a continuation-in-part of Ser. No. 196,795, filed Oct. 14, 1980 (now abandoned) the entire disclosures of which are incorporated herein by reference. Also, this is a continuation-in-part of Ser. No. 388,333, filed June 14, 1982, now abandoned, which is a division of Ser. No. 314,639, filed Oct. 26, 1981 (now abandoned) which, in turn, is a continuation-in-part of said Ser. Nos. 299,413; 270,938; and 196,795.

The novel 3-alkoxy-4-substituted-phenoxy-2,3-unsaturated acids, esters and derivatives thereof of the present invention are represented by the following formulas A', B', C', and D':

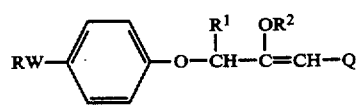
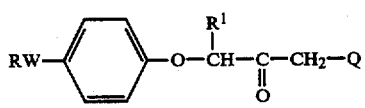
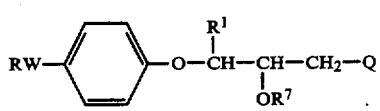
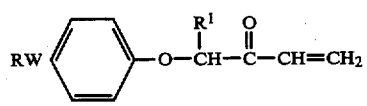

wherein, R is

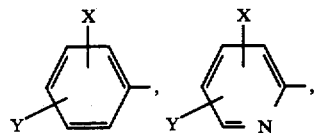

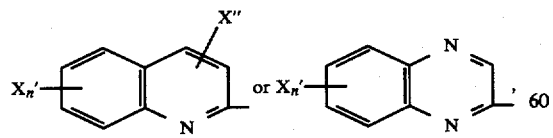

W is O, S, NH or $CH_2$;

each of X and Y is independently selected from hydrogen, bromo, chloro, fluoro, lower alkyl, lower alkoxy, lower alkoxycarbonyl, nitro, cyano, trifluoromethyl, chlorodifluoromethyl, fluoromethyl, chloromethyl and difluoromethoxy;

n is 1 or 2;

each of X' and X" is independently selected from hydrogen, fluoro, chloro, bromo, iodo, trifluoromethyl, methoxy or nitro, provided that both X' and X" cannot be trifluoromethyl, methoxy or nitro;

$R^1$ is hydrogen or lower alkyl;

$R^2$ is lower alkyl;

Q is selected from:

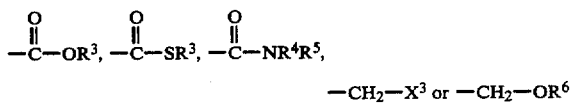

$-CH_2-X^3$ or $-CH_2-OR^6$ in which, $R^3$ is hydrogen, lower alkyl, lower haloalkyl, lower cyanoalkyl, lower hydroxyalkyl, lower alkenyl, lower haloalkenyl, lower alkynyl, lower alkoxyalkyl, dialkoxycarbonylalkyl, lower dialkylaminoalkyl, lower alkylthioalkyl, lower alkylsulfinoalkyl, lower alkylsulfonylalkyl, tetrahydrofuranylmethyl, tetrahydropyranylmethyl, benzyl, halobenzyl, lower alkylbenzyl, lower alkoxybenzyl, phenyl, halophenyl, lower alkoxyphenyl, lower alkylphenyl, cycloalkyl, cycloalkalkyl, N-alkylideneamino, sodium, potassium, magnesium or calcium:

each of $R^4$ and $R^5$ is independently selected from hydrogen, lower alkyl, lower hydroxyalkyl, lower alkoxyalkyl or lower alkylsulfonyl;

$X^3$ is bromo, chloro, fluoro or iodo;

$R^6$ is hydrogen or acyl; and $R^7$ is selected from hydrogen, acyl, phenylacyl, phenoxy acyl, (X,Y-substituted)phenoxy acyl (X-substituted)phenylacyl (X,Y-substituted phenoxy)-phenylacyl, and (X,Y-substituted phenoxy)-(X-substituted phenyl)acyl, wherein X and Y are as defined above.

In the description and claims hereinafter, each of R—$R^7$, n, Q, W, X, X', X", $X^3$ and Y is as defined above, unless otherwise specified.

The compounds of formula (A') wherein Q is

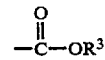

are useful in the controls of weeds and can be produced by the reaction of a phenol of formula (I)

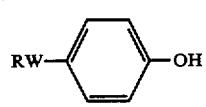

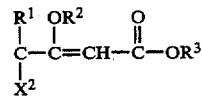

with a 4-halo compound of formula (II) in the presence of a base such as an alkali metal hydroxide or an alkali metal carbonate. The reaction is generally conducted at about room temperature to reflux temperature in an organic solvent such as dimethylformamide (DMF), acetone, tetrahydrofuran (THF), dimethylacetamide (DMA), dimethylsulfoxide (DMSO), or the like using about equimolar amounts of base, phenol of formula (I) and 4-halo compound of formula (II). $X^2$ represents bromo, chloro or iodo.

The thio compounds of formula (A')

(Q being $-\overset{\displaystyle O}{\underset{\|}{C}}-SR^3$)

can be prepared starting with an acid of formula (A')

(Q being $-\overset{\displaystyle O}{\underset{\|}{C}}-OH$)

which is converted into the acid halide and then reacted with a mercaptan. Alternatively, a phenol of formula (I) is reacted with a 4-halo thiolester of the general formula (II) above in the presence of base.

An amide of formula (A')

(Q being $-\overset{\displaystyle O}{\underset{\|}{C}}-NR^4R^5$)

can be prepared by the reaction of an acid halide of an acid of formula (A') with the appropriate amine.

An alcohol of formula (A') wherein Q is $-CH_2-OR^6$ can be prepared by reduction of an acid or ester of formula (A') using, for example, lithium borohydride or lithium aluminumhydride in ether or THF at a low temperature (ice bath). Esters of an alcohol of formula (A') can be prepared by the reaction of an acyl halide or acyl anhydride in pyridine at about room temperature or lower.

A halide of the present invention of formula (A') wherein Q is $-CH_2-X^3$ can be prepared by reaction of an alcohol of formula (A') wherein Q is $-CH_2-OH$ with phosphorus tribromide, phosphorus trichloride, or triphenylphosphine dihalide in acetonitrile.

In another embodiment of the present invention, there is provided 3-oxo derivatives of formula (B') which can be derived from the novel compounds of formula (A').

The compounds of formula (B') are also useful for the control of weeds.

(B')

$$RW-\underset{}{\bigcirc}-O-\underset{R^1}{\underset{|}{CH}}-\underset{\underset{O}{\|}}{C}-CH_2-Q$$

A compound of formula (B') can be prepared by the reaction of a 3-alkoxy compound of formula (A') such as a 3-methoxy compound of formula (A') with an acid such as dilute perchloric acid or acetic acid in an organic solvent such as methylenedichloride, carbontetrachloride or THF. The reaction is usually conducted at about room temperature or lower.

In another embodiment of the present invention, compounds of formula (C') can be prepared by selective reduction of a compound of formula (B') using sodium borohydride in alcohol at low temperature (e.g. ice bath).

(C')

$$RW-\underset{}{\bigcirc}-O-\underset{R^1}{\underset{|}{CH}}-\underset{\underset{OR^7}{|}}{CH}-CH_2-Q$$

Compounds of the formula (C') wherein $R^7$ is an acyl radical can be prepared by selective oxidation of the corresponding hydroxy compound ($R^7$ is hydrogen) by addition of the appropriate acid chloride at a low temperature in a benzene-pyridine, diethyl ether-pyridine or pyridine medium. Alternatively, they may be prepared by addition of the appropriate acid anhydride to the hydroxy compound. The alcohols of formula (C') and carboxylic esters thereof are useful for the control of weeds.

In another embodiment of the present invention, compounds of the formula (D') are provided which are useful for the control of weeds.

(D')

$$RW-\underset{}{\bigcirc}-O-\underset{R^1}{\underset{|}{CH}}-\underset{\underset{O}{\|}}{C}-CH=CH_2$$

The compounds of formula (D') can be prepared by treating an alcohol of formula (D') wherein Q is $-CH_2-OH$ with perchloric acid.

Carboxylic esters of formula (B') wherein Q is $$-\overset{\displaystyle O}{\underset{\|}{C}}-OR^3$$

can be prepared by the following outlined method also:

(III) + (IV) → → $R^3-OH/\Delta^\cdot$ →

$$RW-\underset{}{\bigcirc}-O-\underset{R^1}{\underset{|}{CH}}-\underset{\underset{O}{\|}}{C}-CH_2-\underset{\underset{}{\|}}{\overset{O}{C}}-OR^3$$

The following terms have the meaning indicated as used herein and in the appended claims.

The term "lower alkyl" refers to an alkyl group of one to six carbon atoms.

The term "lower alkoxy" refers to an alkoxy group of one to six carbon atoms.

The term "lower alkoxycarbonyl" refers to an alkoxycarbonyl group of two to six carbon atoms.

The term "acyl" refers to a carboxylic acyl group such as lower aliphatic acyl group of one to six carbon atoms or aryl acyl group of six to twelve carbon atoms. Typical acyl groups include acetyl, benzoyl, p-chlorobenzoyl, and the like.

The term "lower alkenyl" refers to an alkenyl group of two to six carbon atoms with mono-unsaturation such as allyl and n-but-2-enyl.

The term "lower alkynyl" refers to an alkynyl group of two to six carbon atoms with mono-unsaturation such as propargyl.

The term "cycloalkyl" refers to a cycloalkyl group of three to six carbon atoms or to a cycloalkylalkyl group of four to seven carbon atoms.

The term "halo" refers to a bromo, chloro or fluoro group.

The compounds of formula A', B', C', D' are useful for the control of weeds using pre- and/or post-emergent treatments. The compounds can be applied in the form of dusts, granules, solutions, emulsions, wettable powders and suspensions. Application of a compound of the present invention is made according to conventional procedure using from about one-half or less to ten pounds per acre. The application of a compound of the present invention to the "locus" of the weeds includes application to the seeds, the plant (weed) or parts of the plant, or the soil. Methods of preparing herbicidal formulations which can be used with a compound of the present invention are described in the literature along with suitable liquid and solid carrier materials such as in U.S. Pat. Nos. 4,192,669 and 4,163,661 which are incorporated herein by reference. While some of the compounds of the present invention have activity on broad leaf plants, the compounds, in general, demonstrate a higher level of herbicidal activity on the grass weeds. The optimum usage of a compound of the present invention is readily determinable by one of ordinary skill in the art using routine testing such as greenhouse testing and small plot testing.

The term "herbicide", as used herein, refers to an active ingredient which modifies the growth of plants because of phytotoxic or plant growth regulating properties so as to retard the growth of the plant or damage the plant sufficiently to kill it.

The compounds of the present invention demonstrate selective activity as herbicides against grass weeds. Crops such as cotton, sugar beet, soybeans and squash show excellent tolerance. The compounds of the present invention, in general, show a higher level of herbicidal activity when the postemergent method of application is used. Grass plant (weed) species on which the compounds of the present invention show effective herbicidal activity include shattercane, crabgrass, sprangletop, wild oats, bermuda grass, tall fescue, rice, wheat, barley, corn, blue panicum, foxtails, rough bluegrass, winter rye, annual ryegrass, watergrass and Johnsongrass. Application of the active compound prior to the heading stage of the grass weed appears to be most effective.

The compounds of the present invention, in view of their broad spectrum grass weed herbicidal activity, can be advantageously combined with broadleaf weed herbicides for broad spectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamaba, norflurazon, nitrofen, cyanozine, methazole, mefluidide, metribuzin, cycloate, fluometuron, linuron, dalapon, bifenox and alachlor for controlling a broad spectrum of weeds.

The compounds of the present invention are useful for application to sugarcane in order to increase the sucrose content of the sugarcane.

The compounds of the present invention include the isomeric forms and mixtures thereof. Thus, the invention includes the optically active isomers and racemic mixtures. Unless otherwise specified herein, the compounds described in the examples are racemic mixtures.

The following examples are provided to illustrate the practice of the present invention. Temperature is given in degrees centigrade. All parts are by weight unless otherwise indicated. RT means room temperature.

EXAMPLE 1

A mixture of 4-(2-chloro-4-trifluoromethylphenoxy)-phenol (1.16 g), ethyl 4-bromo-3-methoxy-2-pentenoate (prepared in accordance with the procedure of Example 10) (1.74 g) and potassium carbonate (0.73 g) in DMF (5 ml.) is heated at about 130° for 2 hours. Thereafter, DMF is removed. The residue is filtered and washed with methylene dichloride. The filtrate is washed, dried and evaporated to dryness. The oily residue is subjected to prep. thin layer chromatography using 20% ethylacetate/hexane to yield the ethyl ester of 4-[4-(2-chloro-4-trifluoromethylphenoxy)phenoxy]-3-methoxy-2-pentenoic acid, MS m/e 444 (M+).

EXAMPLE 2

A mixture of 4-(2-chloro-4-trifluoromethylphenoxy)-phenol (6.9 mmol.), methyl 4-bromo-3-methoxy-2-pentenoate (8.9 mmol.) and potassium carbonate (1.5 equis.) in acetone (15 ml.) is refluxed for 48 hours. After filtration, the filtrate was concentrated and the residue chromatographed on silica gel using 20% ethylacetate/hexane to give the methyl ester of 4-4-(2-chloro-4-trifluoromethylphenoxy)phenoxy-3-methoxy-1-pentenoic acid.

Some compounds of formula A' which are prepared according to the procedure of the foregoing examples are as follows (Table I and II).

TABLE I $$Y-\underset{X}{\underset{|}{C_6H_3}}-O-C_6H_4-O-CH(R^1)-C(OR^2)=CH-C(O)-OR^3$$

| X | Y | $R^1$ | $R^2$ | $R^3$ |
|---|---|---|---|---|
| H | CF$_3$ | Me | Me | Me |
| H | CF$_3$ | Et | Me | Me |
| Cl | CF$_3$ | Et | Me | Me |
| Cl | CF$_3$ | Me | Et | Me |
| H | OCF$_3$ | Me | Me | Me |
| Cl | OCF$_3$ | Me | Me | Me |
| Cl | Cl | Me | Me | Me |
| NO$_2$ | CF$_3$ | Me | Me | Me |
| H | Br | Me | Me | Et |
| Me | OMe | Me | Me | Me |

TABLE II

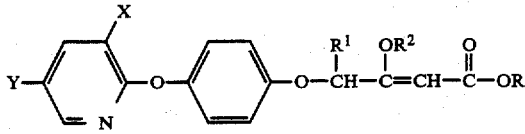

| X  | Y     | R¹ | R² | R³ |
|----|-------|----|----|----|
| Cl | Cl    | Me | Me | Me |
| H  | CF₃   | Me | Me | Me |
| Cl | CF₃   | Me | Me | Me |
| H  | CHF₂  | Me | Me | Me |
| H  | CClF₂ | Me | Me | Me |
| Me | CF₃   | Et | Me | Et |
| F  | CF₃   | Me | Me | Me |
| H  | Br    | Me | Me | Me |
| Cl | Cl    | Me | Et | Et |
| Cl | Cl    | Et | Et | Et |

EXAMPLE 3

A mixture of the methyl ester of 4-[4-(2-chloro-4-trifluoromethylphenoxy)phenoxy]-3-methoxy-2-pentenoic acid (0.5 g), 35% aqueous perchloric acid (5 ml.) and methylene dichloride (5 ml.) is stirred at RT for 4 days. Then the sollution is extracted with methylene dichloride. The residue is purified by prep. thin layer chromatography using 20% ethyl acetate/hexane to yield methyl 4-[4-(2-chloro-4-trifluoromethylphenoxy)phenoxy]-3-oxopentanoate.

The product of Example 1 is treated with aqueous perchloric acid as above to yield ethyl 4-[4-(2-chloro-4-trifluoromethylphenoxy)phenoxy]-3-oxopentanoate, MS m/e 430 (M+).

By use of the foregoing procedure, each of the compounds of Tables I and II are converted into the corresponding 3-oxo-compound of formula (B') such as methyl 4-[4-(4-trifluoromethylphenoxy)phenoxy]-3-oxopentanoate, methyl 4-[4-(4-trifluoromethoxyphenoxy)phenoxy]-3-oxopentanoate, ethyl 4-[4-(2,4-dichlorophenoxy)phenoxy]-3-oxopentanoate, MS m/e 396 (M+), methyl 4-[4-(2,4-dichlorophenoxy)phenoxy]-3-oxopentanoate, methyl 4-[4-(3,5-dichloropyridyloxy)phenoxy]-3-oxopentanoate and methyl 4-[4-(5-trifluromethylpyridyloxy)phenoxy]-3-oxopentanoate.

EXAMPLE 4

A mixture of 4-(2-nitro-4-trifluoromethylphenoxy)phenol (9.36 mm), ethyl 4-bromo-3-methoxy-2-pentenoate (12 mm.) and K₂CO₃ (14 mm.) in acetone (20 ml.) is refluxed for 24 hours. After filtration, the filtrate is concentrated and the oily residue chromatographed on silica gel to yield ethyl 4-[4-(2-nitro-4-fluoromethylphenoxy)phenoxy]-3-methoxy-2-pentenoate.

A solution of the above ethyl ester in 35% perchloric acid and water is stirred at RT for 3 days and then worked up to give ethyl 4-[4-(2-nitro-4-trifluoromethylphenoxy)phenoxy]-3-oxopentanoate.

EXAMPLE 5

To a mixture of lithium aluminum hydride (200 mg) and anhydrous ether (5 ml.) is added dropwise at 0°, a mixture of ethyl 4[4-(2-chloro-4-trifluoromethylphenoxy)phenoxy]-3-methoxy-2-pentenoate (400 mg) and ether (5 ml.). After addition is complete, the mixture is stirred for about 30 minutes. Wet ether and water are added to destroy excess hydride. Filtration and evaporation of filtrate gives 4-[4-(2-chloro-4-trifluoromethylphenoxy)phenoxy]-3-methoxy-2-penten-1-ol.

EXAMPLE 6

A mixture of ethyl 4-[4-(2-chloro-4-trifluoromethylphenoxy)phenoxy]-3-methoxy-2-pentenoate (10 mmol), ethanol (20 ml.) and 1N NaOH (20 ml.) is prepared and then heated at reflux for a few hours to complete the reaction. Removal of solvent gives the sodium salt of 4-[4-(2-chloro-4-trifluoromethylphenoxy)phenoxy]-3-methoxy-2-pentenoic acid. The free acid is obtained by acidification of the salt using dilute H₂SO₄, and extraction with methylene dichloride and evaporation. Other acid salts can be prepared by titrating the free acid with an organic solution of the base, e.g., methanolic solution of potassium methoxide and the like.

EXAMPLE 7

Thionyl chloride (20 ml.) is added to 4-[4-(2-chloro-4-trifluoromethylphenoxy)phenoxy]-3-methoxy-2-pentenoic acid (10 mm.) in anhydrous ether (10 ml.). The mixture is refluxed for a few hours. Then, ether and excess thionyl chloride are removed by vacuum to yield 4-[4-(2-chloro-4-trifluoromethylphenoxy)phenoxy]-3-methoxy-2-pentenoyl chloride.

EXAMPLE 8

To a mixture of 4-[4-(2-chloro-4-trifluoromethylphenoxy)phenoxy]-3-methoxy-2-pentenoyl chloride (10 mm.) and ether (10 ml.) is added methyl mercaptan (12 mm.) and pyridine (1 ml.) at about −20°. The mixture is stirred for about 30 minutes and then allowed to rise to about 0° and stand for about 2 hours. The mixture is then diluted with ether and water and the ether phase separated, washed, dried and solvent removed to give the methythiol ester of 4-[4-(2-chloro-4-trifluoromethylphenoxy)phenoxy]-3-methoxy-2-pentenoic acid.

EXAMPLE 9

A mixture of 4-[4-(2-chloro-4-trifluoromethylphenoxy)phenoxy]-3-methoxy-2-pentenoyl chloride (15 mm) and THF (15 ml.), at 0°, is prepared and then a slight excess of methylamine introduced. The reaction mixture is allowed to stand under nitrogen for about one hour. Then the reaction is allowed to rise to RT and the solvent is removed. The residue is taken up in methylene dichloride, washed, dried and the solvent is removed under vacuum to yield N-methyl 4-[4-(2-chloro-4-trifluoromethylphenoxy)phenoxy]-3-methoxy-2-pentenamide.

EXAMPLE 10

A mixture of ethyl 3-oxopentanoate (20 g) and trimethylformate (5 eq., 94 ml.) in the presence of 6 g of Amberlyst-15 (trademark of Rohm & Haas Corp.) is stirred at RT overnight. After filtration, the filtrate is concentrated and then distilled to give ethyl 3-methoxy-2-pentenoate (19.5 g).

A mixture of the above ethyl ester, N-bromosuccinimide (26.3 g), benzoyl peroxide (0.3 g.) and carbon tetrachloride (100 ml.) is heated to reflux and irradiated with a 150 watt flood lamp until a substantially clear solution is obtained. Thereafter, the reaction is filtered and the filtrate then concentrated and distilled (78°/2 mm) to give ethyl 4-bromo-3-methoxy-2-pentenoate.

EXAMPLE 11

(A) Following the procedure of Example 1, 4-(2-nitro-4-trifluoromethylphenylamino)phenol is reacted with ethyl 4-bromo-3-methoxy-2-pentenoate to give ethyl 4-[4-(2-nitro-4-trifluoromethylphenylamino)-phenoxy]-3-methoxy-2-pentenoate.

(B) Following the procedure of Example 3, the product of part (A) is treated with aqueous perchloric acid to give ethyl 4-[4-(2-nitro-4-trifluoromethylphenylamino)phenoxy]-3-oxopentanoate, MS m/e 512 (M+).

In the same way, there is prepared methyl 4-[4-(2-nitro-4-chlorophenylamino)phenoxy]-3-methoxy-2-pentenoate and methyl 4-[4-(2-nitro-4-chlorophenylamino)phenoxy]-3-oxopentanoate starting with 4-(4-chloro-2-nitrophenylamino)phenol and methyl 4-bromo-3-methoxy-2-pentenoate.

EXAMPLE 12

A spray solution of water/acetone (1:1) and surfactant (1%) was prepared containing (1) the compound of Example 1 (Compound 1) and (2) the second compound of Example 3 (Compound 2) and sprayed (equivalent to 10 lb/acre) on seedlings of foxtail (*Setaria viridis*) and watergrass (*Exhinochlou crusgalli*). Observation two weeks after spraying Compounds 1 and 2 showed 100% herbicidal activity for each of test Compounds 1 and 2. Testing of Compounds 1 and 2 showed no injury to soybeans at 10 lb/acre.

Pre-emergent herbicidal activity of Compound 2 was tested on foxtail, watergrass, shattercane, and wild oats. The average activity was 86% for the four species.

EXAMPLE 13

To a slurry of LiAlH$_4$ (100 mg) in anhydrous ether (20 ml) is added dropwise at 0°, a solution of ethyl 4-[4-(4-trifluoromethylphenoxy)phenoxy]-3-methoxy-2-pentenoate (500 mg) in ether. After addition is complete, the reaction mixture is stirred for about 20 minutes. Excess of the hydride is decomposed using wet ether and water. Filtration and evaporation of filtrate gives the C-1 alcohol, 4-[4-(4-trifluoromethylphenoxy)-phenoxy]-3-methoxy-2-penten-1-ol, MS m/e 440 (M+).

EXAMPLE 14

To a slurry of LiAlH$_4$ (200 mg) in anhydrous ether (15 ml) is added at 0° a solution of ethyl 4-[4-(4-trifluoromethylphenoxy)phenoxy]-3-oxopentanoate (400 mg) in ether (5 ml). After addition is complete, the reaction mixture is stirred at RT for about one hour. Excess of the hydride is decomposed using wet ether and water, the mixture is filtered and filtrate concentrated. The oily product is purified by prep. thin layer chromatography to give 4-[4-(4-trifluoromethylphenoxy)phenoxy]-pentane-1,3-diol, MS m/e 500 (M+).

EXAMPLE 15

To a solution of ethyl 4-[4-(2-nitro-4-chlorophenoxy)-phenoxy]-3-oxopentanoate (600 mg) in absolute ethanol (10 ml) is added at 0°, NaBH$_4$ (300 mg). After addition is complete, the reaction mixture is stirred for about 20 minutes. Then the solution is taken up in CH$_2$Cl$_2$, washed with brine, dried and evaporated to give ethyl 4-[4-(2-nitro-4-chlorophenoxy)phenoxy]-3-hydroxypentanoate.

EXAMPLE 16

To a slurry of LiAlH$_4$ (400 mg) in anhydrous ether (20 ml) is added dropwise at 0°, a solution of ethyl 4-[4-(4-trifluoromethylphenoxy)phenoxy]-3-methoxy-2-pentenoate (1.2 g) in ether (10 ml). After addition is complete, the reaction mixture is stirred for about 10 minutes. Excess hydride is decomposed with wet ether and water. After filtration, the filtrate is concentrated to give the alcohola, 4-[4-(4-trifluoromethylphenoxy)-phenoxy]-3-methoxy-2-penten-1-ol.

The alcohol (600 mg) is stirred with 5 ml of 35% HClO$_4$ in CH$_2$Cl$_2$ (5 ml) for about 20 minutes. The solution is then extracted with CH$_2$Cl$_2$ followed by washing, drying and evaporation. The product is then purified by prep. thin layer chromatography to give 4-[4-(4-trifluoromethylphenoxy)phenoxy]-3-oxo-1-pentene, MS m/e 336 (M+).

EXAMPLE 17

To a solution of ethyl 4-[4-(trifluoromethylphenoxy)-phenoxy]-3-oxopentanoate (450 mg) in ethanol (5 ml) is added NaBH$_4$ (150 mg) at 0°. The resulting mixture is then stirred at 0° for about 10 minutes. The mixture is diluted with CH$_2$Cl$_2$, washed with saturated NaCl solution, dried and evaporated to dryness to give ethyl 4-[4-(4-trifluoromethylphenoxy)phenoxy]-3-hydroxypentanoate, in quantitative yield, MS m/e 398 (M+).

EXAMPLE 18

The process of Example 17 is repeated using ethyl 4-[4-(2-chloro-4-trifluoromethylphenoxy)phenoxy]-3-oxopentanoate (400 mg) and NaBH$_4$ (100 mg) to give ethyl 4-[4-(2-chloro-4-trifluoromethylphenoxy)phenoxy]-3-hydroxypentanoate, MS m/e 432 (M+).

EXAMPLE 19

To a slurry solution of LiAlH$_4$ (200 mg) in anhydrous ether (5 ml) is added dropwise at 0°, a solution of ethyl 4-[4-(2-chloro-4-trifluoromethylphenoxy)phenoxy]-3-methoxy-2-pentenoate (400 mg) in anhydrous ether (5 ml). After addition is complete, the reaction mixture is stirred at 0° for about 10 minutes. Excess hydride is decomposed with wet ether and water. The mixture is filtered and filtrate washed, dried and evaporated to give 4-[4-(2-chloro-4-trifluoromethylphenoxy)phenoxy]-3-methoxy-2-penten-1-ol.

The foregoing alcohol (380 mg) is reacted with 35% HClO$_4$ (4 ml) in CH$_2$Cl$_2$ (4 ml) at RT for 24 hours. The mixture is then extracted with CH$_2$Cl$_2$ and the combined extracts washed, dried and concentrated to dryness. The product is purified by prep. thin layer chromatography to give 4-[4-(2-chloro-4-trifluoromethylphenoxy)phenoxy]-3-oxo-1-pentene, MS m/e 396 (M+).

EXAMPLE 20

A solution of 2-[4-trifluoromethylphenoxy)phenoxy]-propionyl chloride (1.5 g) and methylene chloride (5 ml) is added dropwise at 0° to a solution of 2,2-dimethyl-1,3-dioxane-4,6-dione (680 mg) in methylene chloride (20 ml) containing pyridine (0.7 ml). The resulting mixture is stirred at RT for 2 hours. The reaction mixture is then poured into water, acidified with dilute HCl and extracted with methylene chloride. The combined extracts are washed with brine, dried and evaporated to give 2-[4-(4-trifluoromethylphenoxy)phenoxy]-propionyl meldrum acid, an oil.

The above meldrum acid is treated with n-butanol (20 ml) at 120° for about 4 hours. After aqueous workup, the oily concentrate is purified by prep. thin layer chromatography on silica gel to give n-butyl 4-[4-(4-trifluoromethylphenoxy)phenoxy]-3-oxopentanoate, MS m/e 424 (M+).

EXAMPLE 21

A mixture of 2-nitro-3-trifluoromethyl-4'-hydroxydiphenylamine (1 g), ethyl 4-bromo-3-methoxy-2-pentenoate (990 mg) and potassium carbonate (694 mg) in acetone (10 ml) is refluxed for 24 hours. After filtration and concentration, the crude product is purified by prep. thin layer chromatography on silica gel to give ethyl 4-[4-(2-nitro-4-trifluoromethylanilino)phenoxy]-3-methoxy-2-pentenoate which is treated with 35% $HClO_4$ in methylene chloride to give ethyl 4-[4-(2-nitro-4-trifluoromethylanilino)phenoxy]-3-oxopentanoate, MS m/e 440 (M+).

EXAMPLE 22

Post-emergence activity on the grasses (GR) greenfoxtail, watergrass, shattercane and wild oats was tested for the compound of Examples 13, 14, 17, 18, 20 and 21 (compound No. 3, 4, 5, 6, 7 and 8, respectively) and on the broadleafs (BL) annual morning glory, sesboria, soybean and velvet leaf by spraying at a rate equivalent to 10 lb/acre. The average score is given in percent control.

| Compound No. | GR | BL |
| --- | --- | --- |
| 3 | 100 | 14 |
| 4 | 96 | 8 |
| 5 | 100 | 11 |
| 6 | 100 | 3 |
| 7 | 100 | 7 |
| 8 | 100 | 0 |

EXAMPLE 23

An emulsifiable concentrate was prepared having the following composition (components in percent by weight).

| (VI) | Compound B | 27.78 |
| --- | --- | --- |
| | Igepol CO-530 | 2.67 |
| | Tween 21 | 2.67 |
| | Tween 81 | 2.67 |
| | Corn oil | 64.21 |

Compound B is ethyl 4-[4-(4-trifluoromethylphenoxy)phenoxy]-3-oxopentanoate (90%) purity). Tween 21 is a non-ionic surfactant, polyoxyethylene sorbitan monolaurate and Tween 81 is polyoxyethylene sorbitan monooleate. Tween is a trademark of ICI Americas. Igepal CO-530 is a non-ionic surfactant nonylphenoxypoly(ethleneoxy)ethanol, of GAF, Inc.

| (VII) | Compound C | 29.3 |
| --- | --- | --- |
| | Toximol S | 6.4 |
| | Atlox 8916 TF | 1.6 |
| | Tenneco 500-100 | 62.7 |

Compound C is ethyl 4-[4-(4-trifluromethylphenoxy)phenoxy]-3-hydroxypentanoate (90%) purity).

A spray solution was prepared using 30 parts of concentrate VII, 950 parts of water and 28 parts of non-phytotoxic crop oil and applied to young Johnson grass at the rate of 1.0 lb. per acre. The test plots were observed after two weeks. The application gave 100% control of the Johnson grass.

| (VIII) | Compound B | 27.8 |
| --- | --- | --- |
| | Toximol R | 3.0 |
| | Toximol S | 9.0 |
| | Tenneco 500-100 | 60.2 |

Concentrate VIII was diluted in water and applied at the rate of 2.0 lb. per acre to test specimens, in a greenhouse, of watergrass, green foxtail, shattercane, blue panicum, tallfescue, sprangletop, annual ryegrass, downy brome, wild oats, crabgrass, milo, corn, probred wheat and barley. The average herbicidal activity of two or more evaluations of each of the foregoing grass species was 80% or greater.

Toximol R and S are surfactants of the Stepan Chemical Corporation, Illinois. Atlox 8916F in a surfactant of ICI Americas, Delaware. Tenneco 500-100 is an aromatic solvent of the Tenneco Corporation.

EXAMPLE 24

Flowable formulations were prepared having the following compositions, percent by weight.

| (XI) | (A) | Compound B | 3.00 |
| --- | --- | --- | --- |
| | | Toximol 360A | 3.00 |
| | | Sun 7N (oil) | 30.00 |
| | (B) | Water | 60.85 |
| | | Gelvatol 20/30 | 3.00 |
| | | Kelzan | 0.15 |

Premix (A) was dispersed in high speed blender for about one minute and then Premix (B) was poured into Premix (A) while stirring at high speed. After addition of Premix (B) stirring was continued about 5 minutes.

| (X) | (A) | Compound C | 3.00 |
| --- | --- | --- | --- |
| | | Toximol 360A | 3.00 |
| | | Sun 7N | 30.00 |
| | (B) | Water | 60.85 |
| | | Gelvatol 20/30 | 3.00 |
| | | Darvan No. 1 | 0.15 |

Premix (A) and (B) were combined as described for flowable IX above. Concentration of active ingredient 2.7%.

Sun 7N is a non-phytotoxic oil of the Sun Chemical Company. Gelvatol 20/30 is a polyvinyl alcohol, molecular weight about 10000 of the Monsanto Company. Kelzan is a thickening agent (xanthum gum). Darvan No. 1 is a dispersant of the RT Vanderbilt Company.

EXAMPLE 25

The compound, 2-[4-(4-trifluoromethylphenoxy)-phenoxy]propionyl meldrum acid (V; W is oxygen, R is 4-trifluoromethylphenyl), and $R^1$ is methyl) is reacted with the alcohol $R^3$-OH using the procedure of Example 20 to prepare the respective ester under Table III.

TABLE III

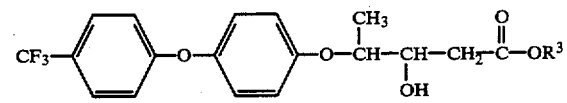

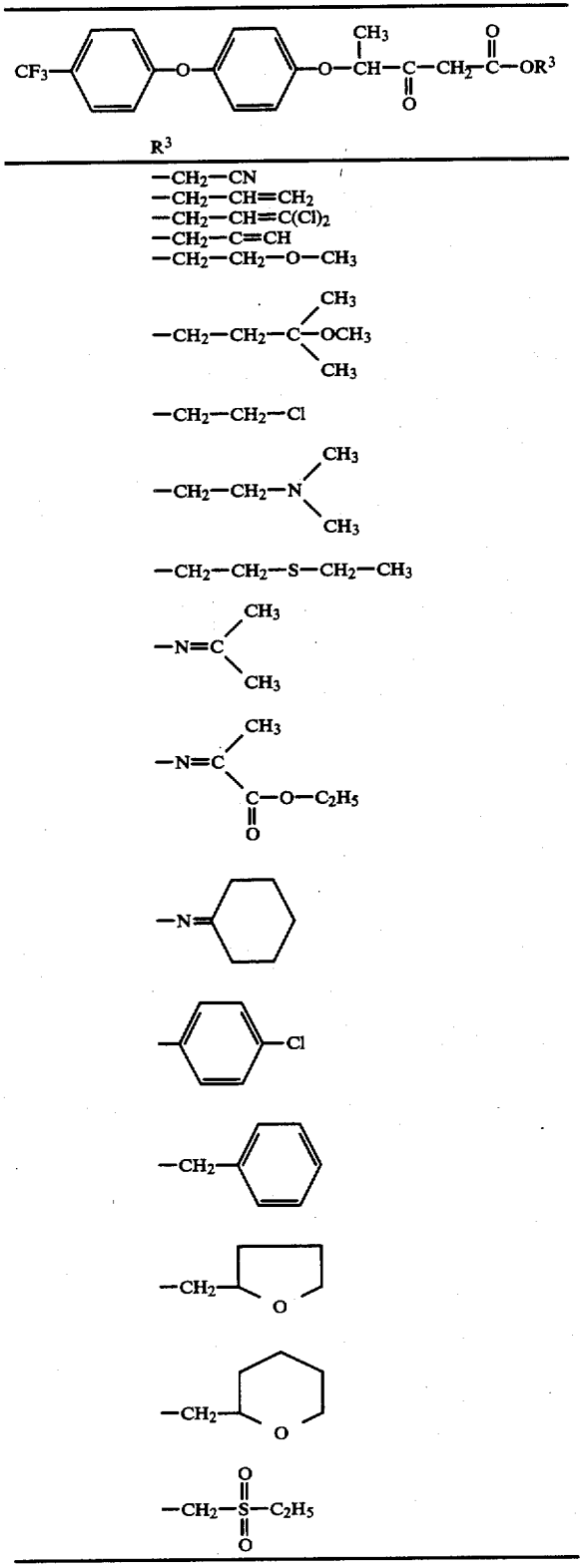

EXAMPLE 26

Following the procedure of Example 17, each of the 3-oxo esters under Table III is reduced using sodium borohydride to yield the respective 3-hydroxy esters of the following formula:

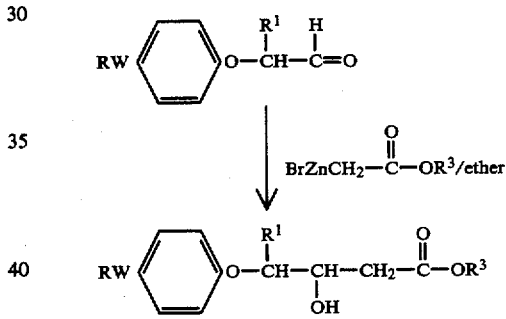

EXAMPLE 27

Ethyl 4-[4-(4-trifluoromethylphenoxy)phenoxy]-3-hydroxypentanoate is reacted with 1.1 equivalent of acetyl chloride and 1.0 equivalent of pyridine in benzene to yield ethyl 4-[4-(4-trifluoromethylphenoxy)-phenoxy]-3-acetoxypentanoate. Similarly, use of n-propanoyl chloride and isopropanoyl chloride yields the respective 3-n-propanoate and 3-isopropanoate.

Carbonates of the 3-hydroxy compounds of formula C' are prepared using the above procedure and 1.1 equivalents of, for example, ethyl chloroformate or methyl chloroformate. The 3-carbonates are also useful herbicides for grass weeds.

In the preparation of the 3-hydroxy compounds of formula C', in addition to reduction of the respective 3-oxo compound of formula B', the 3-hydroxy compounds such as the esters can be prepared by the following outlined method.

$$RW\!\!-\!\!\!\bigcirc\!\!-\!\!O\!-\!\!\underset{\underset{R^1}{|}}{CH}\!-\!\underset{\underset{H}{|}}{C}\!\!=\!\!O$$

$$\downarrow BrZnCH_2-\overset{O}{\overset{\|}{C}}-OR^3/\text{ether}$$

$$RW\!\!-\!\!\!\bigcirc\!\!-\!\!O\!-\!\!\underset{\underset{R^1}{|}}{CH}\!-\!\underset{\underset{OH}{|}}{CH}\!-\!CH_2\!-\!\overset{O}{\overset{\|}{C}}-OR^3$$

EXAMPLE 28

Each of the compounds, methyl 4-[4-(3,5-dichloropyridyloxy)phenoxy]-3-oxopentanoate and methyl 4-[4-(5-trifluoromethylpyridyloxy)phenoxy]-3-oxopentanoate is reacted with $NaBH_4$ by the procedure of Example 17 to yield methyl 4-[4-(3,5-dichloropyridyloxy)phenoxy]-3-hydroxypentanoate and methyl 4-[4-(5-trifluoromethylpyridyloxy)phenoxy]-3-hydroxypentanoate, respectively.

EXAMPLE 29

The process of Example 20 is repeated with the exception of using 2-[4-(6-chloro-2-quinolinyloxy)phenoxy]propionyl chloride as the starting material in place of 2-[4-(4-trifluoromethylphenoxy)phenoxy]-propionyl chloride to yield as the final product, n-butyl 4-[4-(6-chloro-2-quinolinyloxy)phenoxy]-3-oxopentanoate.

By using 2-[4-(6-fluoro-2-quinolinyloxy)phenoxy]-propionyl chloride as the starting material and ethyl alcohol in place of n-butyl alcohol in the process of Example 20, there is obtained ethyl 4-[4-(6-fluoro-2-quinolinyloxy)phenoxy]-3-oxopentanoate which is reduced using $NaBH_4$ in alcohol to yield ethyl 4-[4-(6-fluoro-2-quinolinyloxy)phenoxy]-3-hydroxypentanoate.

EXAMPLE 30

The compound, 6-fluoro-2-(4-hydroxyphenoxy)-quinoxaline, is used as the starting material in Example 1 in place of 4-(2-chloro-4-trifluoromethylpenoxy)-phenol to yield ethyl 4-[4-(6-fluoro-2-quinoxalyloxy)-phenoxy]-3-methoxy-2-pentenoate which is reacted with aqueous perchloric acid by the process of Example 3 to yield ethyl 4-[4-(6-fluoro-2-quinoxalyloxy)phenoxy]-3-oxopentanoate. The 3-oxo ester on reduction with NaBH$_4$ yields the 3-hydroxy ester, i.e., ethyl 4-[4-(6-fluoro-2-quinoxalyloxy)phenoxy]-3-hydroxypentanoate.

EXAMPLE 31

To a suspension of a 2-[4-(5-trifluoromethyl-2-pyridyloxy)phenoxy]propionyl chloride (1.38 mmol) in 5 ml. of methylene chloride, under nitrogen, at 0°, is added, 2,2-dimethyl-1,3-dioxane-4,6-dione (198 mg, 1.38 mmol) followed by pyridine (0.5 ml). The resulting mixture is stirred at 0° for 1.5 hour and at RT for 1 hour. The reaction mixture is poured into 2% HCl in methylene chloride. The organic phase is separated, washed with brine (twice) and dried to give 2-[4-(5-trifluoromethyl-2-pyridyloxy)-phenoxy]propionyl meldrum acid, a red solid.

The above meldrum acid is heated in ethanol (30 ml) to reflux for 2 hours. The reaction mixture is stored at RT overnight. Ethanol is removed by rotoevaporation, and the resulting oily residue is purified by prep. thin layer chromatography (silica gel, 15% ethyl acetate/hexane) to give ethyl 4-[4-(5-trifluoromethyl-2-pyridyloxy)phenoxy]-3-oxo-pentanoate.

nmr (CDCl$_3$) δ 1.22 (t, 3, 7 Hz, CH$_3$CH$_2$O—), 1.52 (d, 3, 7 Hz, CH$_3$CH), 3.63 (s, 2, —C(O)CH$_2$C(O)—), 4.12 (q, 2, 7 Hz, —OCH$_2$CH$_3$), 4.72 (q, 1, 7 Hz, CHCH$_3$), 7.83 (d of d, 1, 9 Hz, 2 Hz, pyridyl 4-H) and 8.38 ppm (br s, 1, pyridyl 6-H).

EXAMPLE 32

To a solution of ethyl 4-[4-(5-trifluoromethyl-2-pyridyloxy)phenoxy]-3-oxopentanoate (175 mg, 0.44 mmol) in 5 ml of absolute ethanol at 0° is added sodium borohydride (32 mg,. 0.84 mmol). The mixture is stirred for 15 minutes, after which it is poured into water and methylene chloride. The aqueous phase is separated and back-extracted with methylene chloride. The combined solvent extracts are washed with brine and dried. Solvent is removed by rotoevaporation, and the residue is purified by prep. thin layer chromatography (silica gel, 25% ethyl acetate/hexane) to yield ethyl 4-[4-(5-trifluoromethyl-2-pyridyloxy)phenoxy]-3-hydroxypentanoate.

nmr (CDCl$_3$δ 1.25 (t, 3, 7 Hz, CH$_3$CH$_2$O—), 1.33 (d, 3, 6 Hz, CH$_3$CH), 2.62 (d, 2, 6 Hz, CH$_2$COO—), 4.13 (q, 2, 7 Hz, CH$_3$CH$_2$O—), 7.77 (d of d, 1, 2 Hz, 9 Hz, pyridyl 4-H) and 8.37 ppm (br s, 1, pyridyl 6-H).

EXAMPLE 33

Following the procedure of Example 31 to 2-[4-(6-fluoro-2-quinoxalyloxy)phenoxy]-propionyl chloride in 10 ml of methylene chloride is added 2,2-dimethyl-1,3-dioxane-4,6-dione (333 mg, 1.15 eq.) and pyridine (0.32 ml, 2 eq.) to give 2-[4-(6-fluoro-2-quinoxalyloxy)-phenoxy]propionyl meldrum acid, which is then heated in methanol (40 ml) to reflux for about 2 hours. The methanol is removed by rotoevaporation, and the residue is purified to yield methyl 4-[4-(6-fluoro-2-quinoxalyloxy)phenoxy]-3-oxopentanoate.

nmr (CDCl$_3$) δ 1.30

(s, 1H, —N=CH—C=N—), 2.20–3.20 (m, 7H, aromatic H), 5.25 (q, 1H, —OCHCH$_3$C(O)—), 6.30 (s, 3H, OCH$_3$), 6.35 (s, 2H, —C(O)CH$_2$C(O)—) and 8.45 ppm (d, 3H, —OCHCH$_3$-C(O)—).

EXAMPLE 34

Post-emergence herbicidal activity on the grasses (GR) green foxtail, watergrass, shattercane and wild oats and on the broadleafts (BL) annual morning glory, mustard, soybean and velvetleaf was tested for the compound of Example 31 and the compound of Example 32 (compounds No. 9 and 10) by spraying seedlings with a solution of water/acetone (1:1), surfactant (1%) and the test compound at a rate equivalent to 10 lb./acre. Scoring was made two weeks after spraying. The average herbicidal activity is given in percent control.

Pre-emergent herbicidal activity of the compounds No. 9 and 10 was tested on the above listed grasses and broadleafs (but with nightshade substituted for soybean) at a rate quivalent to 10 lb./acre. The average score is given in percent control.

| Compound No. | Pre | | Post | |
| --- | --- | --- | --- | --- |
| | GR | BL | GR | BL |
| 9 | 100 | 0 | 100 | 20 |
| 10 | 100 | 0 | 100 | 57 |

EXAMPLE 35

A mixture of 2,3,5-trichloropyridine (2.5 g, 13.7 mm), hydroquinone (3.02 g, 27.4 mm), KOH (3.07 g, 54.8 mm) and DMSO (10 ml) is heated to 160° for 3 hours. The mixture is poured into water, acidified with dilute HCl and extracted with ether. The ethereal solution is washed, dried and evaporated to dryness. The crude product is chromotographed on silica gel to give crystalline 4-(3,5-dichloropyridyloxy)phenol.

The above phenol (1.3 g 5.08 mm), K$_2$CO$_3$ (1.05 g), methyl α-bromopropionate (0.85 ml, 1.5 eq) and acetone (20 ml) is refluxed for 8 hours. The mixture is then filtered and the filtrate concentrated to give oily methyl 2-[4-(3,5-dichloro-2-pyridyloxy)phenoxy]propionate.

The above propionate (1.9 g) in methanol (10 ml) is treated with 10% aqueous NaOH (10 ml) at RT for about 20 minutes. Most of the methanol is removed and the aqueous solution extracted with ether. The aqueous solution is acidified with dilute HCl and then extracted with ether. The combined extracts are dried and evaporated to give crystalline 2-[4-(3,5-dichloro-2-pyridyloxy)phenoxy]propionic acid.

The above acid is reacted with oxalylchloride to obtain the acid chloride which is converted to the meldrum acid and treated with ethanol following the procedure of Example 31 to yield ethyl 4-[4-(3,5-dichloro-2-pyridyloxy)phenoxy]-3-oxopentanoate.

nmr (CDCl$_3$) δ 8.80 (t, 3H, OCH$_2$CH$_3$), 8.50 (d, 3H, 7 Hz, OCH(CH$_3$)), 6.40 (s, 2H, —COCH$_2$CO—) 5.84 (g, 2H, OCH$_2$CH$_3$), 5.32 (q, 1H, OCH(CH$_3$)), 3.04 (m, 4H, —OC$_6$H$_4$O—), 2.34 (d, 1H, 2 Hz, pyridine H), 2.12 (d, 1H, 2 Hz, pyridine H).

In place of 2,3,5-trichloropyridine in the procedure of this Example, there is used 2,3-dichloro-5-trifluoromethylpyridine to yield as the final product, ethyl 4-[4-(3-chloro-5-trifluoromethyl-2-pyridyloxy)phenoxy]-3-oxopentanoate.

EXAMPLE 36

Each of the 3-oxopentanoate products of Example 35 is reduced using NaBH$_4$ in ethanol to yield the 3-hydroxypentanoate product. That is, ethyl 4-[4-(3-chloro-5-trifluoromethyl-2-pyridyloxy)phenoxy]-3-hydroxypentanoate and ethyl 4-[4-(3,5-dichloro-2-pyridyloxy)phenoxy]-3-hydroxypentanoate.

nmr (CDCl$_3$) δ 8.76 (t, 3H, OCH2CH$_3$), 8.70 (d, 3H, 7 Hz, OCH(CH$_3$)), 7.43 (d, 2H, —CH$_2$—CO—), 6.95 (t, 1H, —CH(OH)—), 5.84 (q, 2H, OCH$_2$CH$_3$), 5.84 (m, 2H, OH, OCHCH$_3$), 3.04 (m, 4H, —OC$_6$H$_4$O—), 2.34 (d, 1H, 2 Hz, pyridine H), 2.12 (d, 1H, 2 Hz, pyridine H).

EXAMPLE 37

A mixture of 2,6,7-trichloroquinoxaline (0.8 eq, 3.43 ml.), ethyl 4-(4-hydroxyphenoxy)-3-methoxy-2-pentenoate (1.09 g, 1.2 eq), K$_2$CO$_3$ (568 mg) and CH$_3$CN (20 ml) is refluxed overnight and then filtered. The filtrate is concentrated and taken up in CH$_2$Cl$_2$. The CH$_2$Cl$_2$ solution is washed, dried and evaporated to dryness to yield crystalline enol ether, i.e., ethyl 4-[4-(6,7-dichloro-2-quinoxalyloxy)phenoxy]-3-methoxy-2-pentenoate.

The above enol ether (1.0 g), 35% HClO$_4$ (10 ml) and CH$_2$Cl$_2$ (20 ml) is stirred at RT for 6 days followed by aqueous workup. The product is purified by prep. TLC (20% ethylacetate/hexane) to the 3-oxo ester. Ethyl 4-[4-(6,7-dichloro-2-quinoxalyloxy)phenoxy]-3-oxopentanoate.

nmr (CDCl$_3$) δ 8.80 (t, 3H, OCH$_2$CH$_3$), 8.49 (d, 3H, 7 Hz, —OCHCH$_3$CO—), 6.40 (s, 2H, —C(O)CH$_2$C(O)—), 5.92 (q, 2H, OCH$_2$CH$_3$), 5.25 (q, 1H, —OCH(CH$_3$)CO—), 3.0 (q, 4H, —O—C$_6$H$_4$—O—), 2.27 (s, 1H), 1.99 (s, 1H), 1.44 (s, 1H, quinoxaline H).

The above 3-oxo ester is reduced using NaBH$_4$ in ethanol to yield ethyl 4-[4-(6,7-dichloro-2-quinoxalyloxy)phenoxy]-3-hydroxypentanoate. Ethyl 4-(4-hydroxyphenoxy)-3-methoxy-2-pentenoate is prepared by the reaction of hydroquinone and ethyl 4-bromo-3-methoxy-2-pentenoate in the presence of base in acetone or the like under reflux.

EXAMPLE 38

The procedure of Example 37 is repeated using 2,6-dichloroquinoxaline and methyl 4-(4-hydroxyphenoxy)-3-methoxy-2-pentenoate as the starting materials to yield methyl 4-[4-(6-chloro-2-quinoxalyloxy)phenoxy]-3-methoxy-2-pentenoate which is treated with 35% HClO$_4$ to yield the 3-oxo ester. Methyl 4-[4-(6-chloro-2-quinoxalyloxy)phenoxy]-3-oxopentanoate.

nmr (CDCl$_3$) δ 8.47 (d, 3H, 7 Hz, OCHCH$_3$), 6.37 (s, 2H, —C(O)CH$_2$C(O)—), 6.34 (s, 3H, OCH$_3$), 5.29 (q, 1H, OCHCH$_3$), 2.97 (q, 4H, —O—C$_6$H$_4$—O—), 2.40 (s, 2H), 2.0 (s, 1H), 1.34 (s, 1H, quinoxaline H).

The above 3-oxo ester is reduced using NaBH$_4$ in methanol to prepare the 3-hydroxy ester. Methyl 4-[4-(6-chloro-2-quinoxalyloxy)phenoxy]-3-hydroxypentanoate.

nmr (CDCl$_3$) δ 8.67 (d, 3H, —OCHCH$_3$C—), 7.37 (d, 2H, —CH$_2$—CO—), 6.79 (t, 1H, —CHOH—), 6.29 (s, 3H, OCH$_3$), 5.71 (m, 2H, —OCHCH$_2$—, —CHOH), 1.35 (s, 1H, quinoxaline H).

EXAMPLE 39

To a solution of D(—)-2-[4-(3,5-dichloro-2-pyridyloxy)phenoxy]propionic acid (500 mg, 1.52 mm) in ether (10 ml) and DMF (1 drop) is added oxalylchloride (0.8 ml, 2 eq). The mixture is stirred at RT for one hour and then concentrated to dryness to give the acyl chloride.

The acyl chloride in CH$_2$Cl$_2$ (10 ml) is added at 0° to a solution of 240 mg of 2,2-dimethyl-1,3-dioxane-4,6-dione (IV) in CH$_2$Cl$_2$ (10 ml) containing pyridine (0.2 ml). The mixture is stirred at 0° for one hour and then at RT for one hour. The mixture is taken up in CH$_2$Cl$_2$, washed with dilute HCl and water, dried and evaporated to dryness to give 2-[4-(3,5-dichloro-2-pyridyloxy)phenoxy]propionyl meldrum's acid. The meldrum's acid is reacted with ethanol to give D(+)ethyl 4-[4-(3,5-dichloro-2-pyridyloxy)phenoxy]-3-oxopentanoate. $[\alpha]_{25}{}^D = +11.58$ in CHCl$_3$.

Examples of herbicides, in addition to the herbicides described hereinabove, which can be combined with a compound of the present invention in order to control a broad spectrum of weeds are described by W. T. Thomson, "Agricultural Chemicals—Book II Herbicides", Thomson Publications, Fresno, Calif., U.S.A., 1981–82 Revision, the entire disclosure of which is incorporated herein by reference.

EXAMPLE 40

To a solution of methyl 2-[4-(3-chloro-5-trifluoromethyl-2-pyridyloxy)phenoxy]propionate (1.75 g) in methanol (15 ml) is added potassium hydroxide (1.0 g) in water (10 ml). The resulting mixture is stirred at RT until a clear solution is obtained (about 20 min). Most of the methanol is removed, and the aqueous solution is acidified with dilute HCl and extracted with ether. The combined ether extracts are dried and concentrated to dryness to give 2-[4-(3-chloro-5-trifluoromethyl-2-pyridyloxy)-phenoxy]propionic acid.

To the above acid (2.1 g) in ether (20 ml) containing DMF (3 drops) is added, dropwise, oxalyl chloride (1 ml). The mixture is stirred at RT for 1 hour, then concentrated to dryness to give 2-[4-(3-chloro-5-trifluoromethyl-2-pyridyloxy)phenoxy]propionic acid chloride.

The above acid chloride in methylene chloride (10 ml) is added, dropwise, at 0° to a solution of meldrum's acid (0.84 g) in methylene chloride (20 ml) containing pyridine (1 ml). After addition, the mixture is stirred at 0° for 1 hour, then at RT for 1.5 hour. It is then poured into water and extracted with methylene chloride. The combined extracts are washed with dil. HCl and with water, dried and evaporated to give an oily residue which is purified by prep. TLC to give ethyl 4-[4-(3-chloro-5-trifluoromethyl-2-pyridyloxy)phenoxy]-3-oxopentanoate.

nmr (CDCl$_3$) δ 8.80 (t, 3H, —OCH$_2$CH$_3$), 8.49 (d, 3H, 7 Hz, —OCH(CH$_3$)), 6.40 (s, 2H, —COCH$_2$CO—), 5.90 (q, 2H, —OCH$_2$CH$_3$), 5.30 (q, 1H, —OCH(CH$_3$)), 3.03 (m, 4H, aromatic H), 2.09–1.80 (d, d, 2H, pyridine H).

EXAMPLE 41

Ethyl 4-[4-(3-chloro-5-trifluoromethyl-2-pyridyloxy)phenoxy]-3-oxopentanoate (680 mg) is reduced using NaBH$_4$ (60 mg) in ethanol (10 ml) to yield ethyl 4-[4-(3- chloro-5-trifluoromethyl-2-pyridyloxy)phenoxy]-3-hydroxypentanoate.

nmr (CDCl$_3$) δ 8.70 (t, 3H, —OCH$_2$C$\underline{H}_3$), 8.67 (d, 3H, 7 HZ, —OCH(C$\underline{H}_3$)), 7.29 (d, 2H, —C$\underline{H}_2$CO—), 5.84 (q, 2H, —OC$\underline{H}_2$CH$_3$), 5.84 (m, 1H, —OC$\underline{H}$(CH$_3$)), 3.00 (m, 4H, aromatic H), 2.07 (d, H, 2 Hz, pyridine H), 1.80 (d, 1H, 2 Hz, pyridine H).

EXAMPLE 42

Preparation of methyl 4-[4-(4-trifluoromethylphenoxy)phenoxy]-3-oxopentanoate 15 g of crude [4-(4-trifluoromethylphenoxy)phenoxy]meldrum acid prepared in accordance with the method of Examples 20 and 25 were refluxed in 150 ml of methanol for two hours, allowed to stand overnight and again refluxed an additional four hours. The solvent was evaporated. The product was dissolved in equal amounts of hexane and diethyl ether, washed with water, dried over MgSO$_4$, its volume reduced (RV) to 12 g and passed through a 200 g silica gel column in a 9:1 hexane/ethylacetate solution. 1.6 grams of pure product were recovered, which, upon analysis, were found to be the above methyl ester.

EXAMPLE 43

Preparation of ethyl 4-[4-(4-trifluoromethyl,2-chlorophenoxy)phenoxy]-3-oxopentanoate 6 g of the crude corresponding meldrum acid, prepared in accordance with the method of Examples 20 and 25, were diluted with approx. 150 ml of ethanol. The mixture was refluxed for 4 hrs. and poured into water, acidified with HCl and extracted with 150 ml of ethylacetate three times. The organic layer was dried over MgSO$_4$ and concentrated by vacuum evaporation. The crude, brown product was purified by TLC using 9:1 hexane/ethylacetate. 1.9 g of product were thus obtained along with 1.5 g of the meldrum acid. The product was identified as the above ethyl ester.

EXAMPLE 44

Preparation of propionyl meldrum acid 4.2 g of oxalyl chloride were added dropwise and under stirring to a solution of 5.25 g of 2-[4-(4-trifluoromethylphenoxy)phenoxy]propionic acid in approx. 75 ml of methylene chloride in the presence of a small amount of dimethyl formamide catalyst. The mixture was stirred for 1 hr, and then the solvent end excess oxalyl chloride were removed by vacuum evaporation. The product of this reaction, 5.89 g of 2-[4-(4-trifluoromethyl-phenoxy)phenoxy]propionyl chloride dissolved in 35 ml of methylene chloride, was added dropwise at 0° C. to a solution of 2,2-dimethyl-1,3-dioxane-4,6-dione (3.6 g) in 70 ml of methylene chloride containing approx. 3 ml pyridine. The resulting mixture was stirred at room temperature for 2 hrs, poured into water and acidified with 2M HCl. The product was extracted three times with 150 ml of methylene chloride and dried over MgSO$_4$. The organic layer was concentrated by vacuum to produce 9 g of brown crude meldrum acid.

EXAMPLE 45

Preparation of ethyl 4-[4-(5-trifluoromethyl-2-pyridyloxy)phenoxy]-3-oxopentanoate 15 equivalents of (13.5 g) CrO$_3$ in pyridine, were stirred in 100 ml of methylene chloride and 3.1 g of the ethyl-3-hydroxy ester (prepared according to Exs 35 and 36) overnight. The resulting mixture was transferred to a separation funnel with methylene chloride, washed with NaHCO$_3$, H$_2$O, 0.5M HCl and brine and then dried (over MgSO$_4$) RV to 1.95 g. The crude product, separated by silica gel chromatography yielded 1.45 g of pure product, which was identified as the above ethyl ester.

EXAMPLE 46

Preparation of ethyl 4-[4-(5-trifluoromethyl-2-pyridyloxy)phenoxy]-3-hydroxypentanoate 1 g of the methylhydroxypentanoate of the above compound was mixed with 35 ml ethanol and refluxed in the presence of a small amount (2–3 drops) of sulfuric acid for 12 hours. A product slowly formed which was purified by prep. TLC and identified as the above ethyl hydroxy ester.

EXAMPLE 47

Preparation of Butyl 4-[4-(5-trifluoromethyl-2-pyridyloxy)phenoxy]-3-hydroxypentanoate 10 g of the methylhydroxyester of this compound (prepared in accordance with the procedure of Example 28) in 140 ml butanol were refluxed for 7 hrs. Most of the butanol was evaporated and the remaining mixture was taken up in methylene chloride, was washed with water, sodium bicarbonate, 0.5M HCl and brine, dried over magnesium sulfate and concentrated (RV) to 10.96 g. The product was purified by silica gel chromatography and identified as the above butyl hydroxyester (99% yield).

EXAMPLE 48

Preparation of hydroxyethyl 4-[4-(4-trifluoromethylphenoxy)phenoxy]-3-hydroxypentanoate 2.21 g. of the corresponding hydroxyethyl-3-oxo ester (prepared according to Ex. 50) were mixed with 1.2 g NaBH$_4$ in 20 ml of ethylene glycol at 0° C. After 20 min. the reaction had reached about 50% completion. The mixture was worked up and the procedure was repeated. The mixture was allowed to rest for 2 hrs the second time. The mixture was taken up in methylene chloride and water and washed with brine and dried over MgSO$_4$ RV to 1.62 g. The product was separated by silica gel column chromatography and was characterized as the above compound.

EXAMPLE 49

Preparation of butyl 4-[4-(5-trifluoromethyl-2-pyridyloxy)phenoxy]-3-oxopentanoate 6.9 g of the corresponding butyl-hydroxypentanoate (prepared according to the procedure of Ex. 47) were dissolved in methylene chloride and added to a methylene chloride solution of 10.5 g of CrO$_3$ and 11 ml of pyridine (150 ml CH$_2$Cl$_2$ and stirred at room temperature for 7 hrs. Reaction was 50% complete. The mixture was washed with water, sodium bicarbonate, 0.5M HCl and brine and dried over MgSO$_4$, RV to 4.54 g. The product was separated by silica gel chromatography and identified as the above butyl ester.

EXAMPLE 50

Preparation of hydroxyethyl 4-[4-(4-trifluoromethylphenoxy)phenoxy]-3-oxopentanoate 12.8 g of the corresponding meldrum acid (prepared in accordance with the method of Example 44) were refluxed with 140 ml ethyleneglycol for ½ hr. After standing overnight, the refluxed mixture was heated in a 100° C. oil bath for 4 hrs. Thereafter, it was placed in a separation funnel with H$_2$O, and ether. An emulsion was formed, which was cleared with brine. The water layer was extracted with diethylether three times and the ether layer was collected, washed with water and brine and dried over MgSO$_4$ RV to 11.6 g. The product was purified by silica gel chromatography (200 g) using hexane/ethylacetate (1:1) as the eluant and identified as the above hydroxyethyl ester.

EXAMPLE 51

Preparation of methyl 4-[4-(4-trifluoromethylphenoxy)phenoxy]-3-hydroxypentanoate The corresponding methyl-3-oxo ester (2.5 g) was dissolved in 20 ml of absolute ethanol (in an ice bath) and 1.34 g of NaBH$_4$ was added. The solution was stirred for 30 min. then taken up in methylene chloride, washed with brine, dried and evaporated to 1.85 g. The crude product was purified by silica gel chromatography and identified as the object methyl 3-hydroxy ester.

EXAMPLE 52

Preparation of methyl[4-(5-acetyl-2-pyridyloxy)phenoxy)phenoxy]-propionate 4.7 g of 3 acetyl-5-chloropyridine, 5.37 g of methyl(4-hydroxyphenoxy)propionate and 5.67 g of K$_2$CO$_3$ were refluxed in methyl cyanide for 4 hrs. 18-crown 6 (1,4,7,10,13,16-hexaoxacyclooctadecane) was added to speed up the reaction and the mixture was refluxed for an additional 5 hrs, but reaction was still incomplete. The mixture was decanted into a separation funnel, washed with H$_2$O, 5% NaOH, H$_2$O and brine and dried over MgSO$_4$ RV to 4.7 g. The product was purified by silica gel/hexaneethylacetate chromatography and identified as the above methyl ester.

EXAMPLE 53

Preparation of Ethyl 4-[4-(3-chloro-5-trifluoromethyl-2-pyridyloxy)phenoxy]-3-oxopentanoate Pyridine (16 ml) was added to a mixture of CrO$_3$ (10 g) in 120 ml methylene chloride dropwise and stirred for 20 min. 6 g of the corresponding ethyl 3-hydroxy ester were dissolved in methylene chloride and added to the pyridine mixture. The resultant mixture was stirred for 1.25 hrs and decanted in a separation funnel, washed with methylene chloride, dilute NaHCO$_3$, 0.5M HCl, water and brine and dried over MgSO$_4$ RV to 6.1 g. The product was separated by silica gel column chromatography (hexane/ethylacetate 4:1) and identified as the above ethyl ester.

EXAMPLE 54

Preparation of Butyl 4-[4-(3-chloro-5-trifluoromethyl-2-pyridyloxy)phenoxy]-3-hydroxypentanoate The corresponding ethyl hydroxy pentanoic acid ester (3.5 g) was refluxed in n-butanol (100 ml) for 7 hours in the presence of a small amount (4–8 drops) of H$_2$SO$_4$. The excess butanol was evaporated. The mixture was taken up in methylene chloride, and washed with water, NaHCO$_3$, and brine and its volume was reduced to 3.4 g. The product was purified by silica gel column chromatography using 4:1 hexane/ethyl acetate and identified as the butyl ester of 4(3-chloro,5-trifluoromethyl-2-pyridyloxy)phenoxy-3-hydroxypentanoic acid.

EXAMPLE 55

Preparation of methyl 4-[4-(3-chloro-5-trifluoromethyl-2-pyridyloxy)phenoxy]-3-hydroxypentanoate 10 g of the corresponding ethyl ester were refluxed in 120 ml of methanol (in the presence of 4 drops of H$_2$SO$_4$) for 6 hours. Four more drops of H$_2$SO$_4$ were added and the mixture was refluxed for an additional 8 hrs and RV to 9.35 g. The product was identified as the above methyl-3-hydroxypentanoate.

EXAMPLE 56

Preparation of methyl[4(3-chloro-5-trifluoromethylpyridyloxy)-phenoxy]-3-oxopentanoate The product of Example 55 (9.35 g) was stirred with 6 eg of CrO$_3$ in pyridine in 250 ml of methylene chloride over a weekend. The mixture was washed with NaHCO$_3$, 0.5M HCl, water and brine and dried over MgSO$_4$ to 4.8 g. The product was purified by silica gel column chromatography using 9:1 hexane/ethyl acetate and identified as the methyl 3-oxo ester (2.86 g).

EXAMPLE 57

Preparation of meldrum's acid from recrystallized precursor 23.10 g meldrum's acid, 23.7 ml pyridine and 96 ml methylene chloride are added in a 250 ml flask filled with a thermometer, condenser and addition funnel. Contents are cooled to 0° C. in an ice bath (using acetone). 56.2 g of [4-(4-trifluoromethyl phenoxy)phenoxy]propionyl chloride diluted in 20 ml methylene chloride were slowly added. The mixture was worked up with 100 ml of water (in ice), 100 ml of dilute HCl and again 100 ml of H$_2$O twice (in ice) and stripped at room temperature for half an hour. The product is an orange oil.

The oil was decanted and recrystallized by ethyl acetate addition and standing overnight. It was then stripped at room temperature for 45 min. One half of it was recrystallized in 40% diethyl ether/hexane and the remaining half in 40% carbon tetrachloride/hexane. Both aliquots recrystallized immediately. After overnight refrigeration, the crystals were rinsed with cold solvent and stripped on aspirator at high vacuum to obtain 2.29 g. The aqueous layer was again acidified (to pH 3) and methylene chloride was added. The organic layer was stripped by aspirator at high vacuum at 30° C. to yield 0.09 g of acid. The product weighed 2.38 g and contained 75.1% of a keto ester.

The keto ester and ethylacetate (1-3 g) were scaled up with 20 ml ethyl acetate and water. The pH was adjusted to 9 and the mixture was twice washed with (2×20 ml) water. The first wash was extracted with ethyl acetate at pH 3 yielding a total of 0.66 g of acid. The second wash extracted with ethylacetate yielded 0.06 g of acid. The total recovery was 2.89 g of product containing 23% keto ester, identified as 4-[4-(4-trifluoromethylphenoxy)phenoxy]propionyl meldrum' acid.

EXAMPLE 58

Preparation of hydroxyethyl 4-[4-(3-chloro-5-trifluoromethyl-2-pyridyloxy)phenoxy]-3-oxopentanoate The meldrum acid of Example 57 was heated in an oil bath at 100° C. for 2.5 hours with 20 ml of ethanol. The reaction was about 50% complete. The volume was reduced to 2.14 g and the mixture was reheated for 4 hours after further addition of 20 ml of ethanol. The mixture was water- and brine-washed and dried over $MgSO_4$ and the volume was reduced to 0.97 g. The product was identified as the above hydroxyethyl ester.

EXAMPLE 59

Preparation of Methyl 4-[4-(5-trifluoromethyl-2-pyridyloxy)phenoxy]-3-acetoxypentanoate 5 g of methyl 4-[4-(5-trifluoromethyl-2-pyridyloxy)phenoxy]-3-hydroxypentanoate were dissolved in 35 ml of methylene chloride at 0° C. 0.9 ml of acetyl chloride and then 0.94 ml of triethylamine were added dropwise under nitrogen. After 18.5 hours of standing at room temperature and three hours of reflux, an additional 0.9 ml of acetyl chloride and 0.94 ml of triethylamine were added. The mixture was washed with water dilute acid and brine. The product was purified using silica gel chromatography and identified as the above methyl-3-acetoxy ester.

EXAMPLE 60

Preparation of ethyl 4-[4-(4-trifluoromethylphenoxy)phenoxy]-3-formoyloxypentanoate 4 g of ethyl 4-[4-(4-trifluoromethylphenoxy)phenoxy]-3-hydroxypentanoate in formic acid were heated to 60° C. for 6 hours and to 65° C. for an additional 3 hours (approx. 80% complete reaction) Methylene chloride and $H_2O$ were added to the mixture after transferring to a separation funnel. The methylene chloride layer was washed with water, $NaHCO_3$, water and brine, dried over $MgSO_4$ and its volume reduced to 3.8 g. The product was purified by silica gel chromatography (hexane/ethyl acetate) and identified as the above methyl formoyloxypentanoate ester with an overall yield of 60%.

EXAMPLE 61

Preparation of ethyl 4-[4-(4-trifluoromethylphenoxy)phenoxy]-3-benzoyloxypentanoate 2.5 g of ethyl 4-[4-(4-trifluoromethylphenoxy)phenoxy]-3-hydroxypentanoate were refluxed with 1.2 min. of benzoyl chloride in 60 ml of methylene chloride in the presence of 1.3 ml of triethylamine for 1(½) hours. The product was diluted with methylene chloride washed with water, 1M HCl and brine and dried over $MgSO_4$. The product was purified by silica gel chromatography (total yield 92%) and was identified as a mixture of two stereoisomers of the above ethyl benzoyloxypentanoate.

EXAMPLE 62

Preparation of ethyl 4-[4-(4-trifluoromethylphenoxy)phenoxy]-3-acetoxypentanoate 4 g of the corresponding ethyl-3-hydroxypentanoate, 1.6 ml of acetyl chloride and 1.8 ml of triethylamine in 50 ml of methylene chloride are refluxed for a total of 9 hours. The mixture is diluted with methylene chloride, washed with water, 1M HCl, and brine and RV to 2.7 g. The resulting crude product was purified with prep. silica gel TLC and identified as the above ethyl-3-acetoxy ester.

EXAMPLE 63

Preparation of ethyl 4-[4-(4-trifluoromethylphenoxy)phenoxy]-3-acetoxypentanoate 0.9 g of the corresponding ethyl hydroxyester was added in a flask under nitrogen with 10–15 ml of diethyl ether. The flask was chilled in brine with dry ice to −10° C. 0.283 ml of pyridine and 0.183 ml of acetyl bromide were added. The precipitate was filtered, rinsed with diethyl ether and discarded. The filtrate and rinse were combined, extracted several times with ice water-diethyl ether solution, dried over $MgSO_4$, and concentrated by evaporation. The product was purified by silica gel chromatography and identified as the desired ethyl acetoxyester.

EXAMPLE 64

Preparation of ethyl 4-[4-(4-trifluoromethylphenoxy)phenoxy]-3-formoyloxypentanoate (a) Preparation of formyl acetate 15 g of sodium formate (dried under vacuum over a 60° oil bath) were finely ground and introduced in a flask under nitrogen. 15 ml of diethyl ether were added. The mixture was chilled in an ice-salt bath to 5° C. Acetyl chloride was added dropwise and the mixture was allowed to reach room temperature (kept at about 25° C.), and stirred for 4 hours then sealed and stirred overnight. The precipitate was filtered, rinsed with diethylether and discarded. The supernatant and rinse were combined and their volume reduced. The reduced volume oil was distilled and the lightest fraction was used, containing formylacetate slightly contaminated with formic and acetic acid.

(b) Preparation of the Object Ester 1.2 g ethyl 4-[4-(4-trifluoromethylphenoxy)phenoxy]-3-hydroxypentanoate was dissolved in 12 ml diethyl ether, transferred to a flask under nitrogen and chilled in an ice bath. 0.36 ml pyridine were added and stirred for 15 minutes. Approximately 0.23 ml (0.26 g) of the distillate fraction produced in (a) above was added and stirred 15 minutes. An additional 0.13 ml of the distillate fraction produced in (a) above, and 4.5 mM pyridine were added and stirred for a half hour. The mixture was brought to room temperature. 2½ hours after the second distillate addition, another 0.13 ml of the distillate fraction was added and the mixture was kept at room temperature for 1 hour. The precipitate was decanted, additional ether was added, and the supernatant was extracted four times with (4×10 ml of) ice water. The ether layer was dried over MgSO$_4$ and refrigerated. The product was filtered dried over MgSO$_4$, rinsed with diethylether and the filtrate and rinse were volume-reduced to an oil. The product was purified by silica gel chromatography (90.10 hexane/ethyl acetate) and identified as the formate ester of the starting ethyl hydroxypentenoate material.

EXAMPLE 65

Preparation of the 3-chloroacetoxyester of ethyl 4-[4-(4-trifluoromethylphenoxy)phenoxy]pentanoate 0.9 g of ethyl 4-[4-(4-trifluoromethylphenoxy)-phenoxy]-3-hydroxypentanoate was mixed with diethyl ether (10 ml) and placed in an ice bath. 0.485 ml of pyridine followed by 0.77 g of chloroacetic anhydride were added. The ice bath was removed and the mixture was stirred, allowed to attain room temperature, and stirred over a weekend. The solid was decanted and discarded. The supernatant was extracted with ice-ether solution (10 ml) four times. The ether solution was dried over MgSO$_4$, filtered and reduced to oil. The crude product was purified by silica gel chromatography and identified as the object ethyl-3-chloroacetoxyester.

EXAMPLE 66

Preparation of the 3-(2,2-dichloropropanoate)ester of ethyl 4-[4-(4-trifluoromethylphenoxy)phenoxy]-3-hydroxypentanoate 600 mg of the corresponding hydroxyester (85% pure) were dissolved in 20 ml of benzene containing pyridine (0.3 ml). 0.3 ml of 2,2-dichloropropionyl chloride was added dropwise at 0° C. The resulting mixture was stirred at room temperature for 4 hours, then taken up in ether. The organic phrase was washed, dried and concentrated to dryness. The crude product was purified by prep. thin layer chromatography, and identified as the above 2,2-(dichloro)propionyl ester.

EXAMPLE 67

Preparation of ethyl 4-[4-(3-chloro-5-trifluoromethyl-2-pyridyloxy)phenoxy]-3-acetoxypentanoate The corresponding 3-hydroxyester was used as starting material. 500 mg of the hydroxyester were dissolved in 1.5 ml of benzene containing 0.2 ml pyridine. Acetyl-chloride (0.15 ml) was added dropwise and the resulting mixture was stirred at room temperature for 4 hours. It was then poured into water and extracted with ether. The combined extracts were washed, dried over MgSO$_4$ and the solvent evaporated to dryness. The product was purified by silica gel chromatography and identified as the above acetoxy ester.

EXAMPLE 68

Preparation of the 3-[4-(2,4-dichlorophenoxy)butanoate]ester of ethyl 4-[4-(4-trifluoromethylphenoxy)phenoxy]-3-hydroxypentanoate To ethyl 4-[4-(4-trifluoromethylphenoxy)phenoxy]-3-hydroxypentanoate (3.0 g) in diethyl ether (5 ml), chilled in ice bath, is added 4-(2,4-dichlorophenoxy)-butanoic acid chloride (1.75 g) in diethyl ether (5 ml), pyridine (0.15 mole) and diethyl ether (10 ml). After addition in complete, the reaction mixture is allowed to rise to room temperature. After about 10 minutes, the mixture is washed with water and the organic layer dried over magnesium sulfate and concentrated under vacuum. The concentrate is chromatographed on silica gel using hexane/ethyl acetate (4/1) and fractions 3–6 collected to give the 3-[4-(2,4-dichlorophenoxy)-butanoate]ester of ethyl 4-[4-(4-trifluoromethylphenoxy)phenoxy]-3-hydroxypentanoate, structure confirmed by mass spec.

EXAMPLE 69

Preparation of the 3-[5-(2-chloro-4-trifluoromethylphenoxy)-2-nitrobenzoate]ester of ethyl 4-[4-(4-trifluoromethylphenoxy)phenoxy]-3-hydroxypentanoate Following the foregoing procedure, 5-(2-chloro-4-trifluoromethylphenoxy)-2-nitrobenzoic acid chloride is reacted with ethyl 4-[4-(4-trifluoromethylphenoxy)-phenoxy]-3-hydroxypentanoate to give the 3-[5-(2-chloro-4-trifluoromethylphenoxy)-2-nitrobenzoate]-ester, purified by column chromatography using hexane/ethyl acetate (4/1), structure confirmed by mass spec.

EXAMPLE 70

Preparation of 4-[4-(3-chloro-5-trifluoromethyl-2-pyridyloxy)phenoxy]-3-formoyloxypentanoate 600 mg of ethyl 4-[4-(3-chloro,5-trifluoromethyl-2-pyridyloxy)phenoxy]-3-hydroxypentanoate were dissolved in 5 ml of pyridine. Excess formic acetic anhydride was added (prepared in situ as in Example 64 but undistilled) in portions. Gas evolution occurred during and immediately following the addition of each portion. After several hours, ice was added and the mixture was allowed to stand for 30 min. Thereafter, it was poured into 5% HCl and ether. The organic phase was separated and washed with 2M Na$_2$CO$_3$, then brine, and dried over sodium sulfate. The solvent was removed and the residue (about 0.6 g.) was purified by prep. thin layer chromatography using 15% ethylacetrate/hexane solvent, and identified as the desired formate ester (0.41 g.).

EXAMPLE 71

Preparation of 4-[4-(4-trifluoromethylphenoxy)phenoxy]-3-hydroxypentanoic acid

A mixture of 7.0 g of ethyl 4-[4-(4-trifluoromethyl-phenoxy)phenoxy]-3-hydroxypentanoate and 1.74 g of 85% KOH in 30 ml ag. methanol was stirred at room temperature for 1.5 hrs. The mixture was concentrated, poured into water and acidified. The product was dissolved in ether, washed with brine, dried over MgSO4 and vacuum evaporated to yield 6.0 of product which was identified as the subject 3-hydroxypentanoic acid.

EXAMPLE 72

The compounds of Examples 63, 64, 65, 66, 67, 68, and 69 and ethyl 4-[4-(2-chloro-4-trifluoromethylphenoxy)-phenoxy]-3-methoxy pentanoate (EPPMOP) were tested for both pre-emergence and post-emergence activity against the broadleafs (BL): annual morning glory, Florida broadleaf mustard, Mitchell soybean (post-only), tomato (pre-only) and the grasses (GR) green foxtail, barnyard grass, shattercane and wild oats by spraying an equivalent of 10 lbs/acre. The results are set forth below in percent control:

| Compound | PRE | | POST | |
|---|---|---|---|---|
| | GR | BL | GR | BL |
| Ex. 68 | 100 | 74 | 100 | 60 |
| Ex. 69 | 90 | 59 | 98 | 85 |
| Ex. 63 | 98 | 0 | 100 | 3 |
| Ex. 64 | 95 | 0 | 100 | 5 |
| Ex. 65 | 98 | 6 | 98 | 7 |
| Ex. 67 | 96 | 0 | 100 | 15 |
| Ex. 66 | 15 | 7 | 50 | 10 |
| EPPMOP | 100 | 0 | 99 | 23 |

EXAMPLE 73

To a solution of (R)-2-[4-(4-trifluoromethylphenoxy)-phenoxy]-propanoic acid (1.62 g., 4.96 mm), ether (20 ml) and dimethylformamide (about 2 drops) is added slowly oxalyl chloride (0.8 ml., 2 eq.). After addition of oxalyl chloride, the reaction mixture is stirred at room temperature for one hour. The mixture is then concentrated to give the acid chloride, (R)-2-[4-(4-trifluoromethylphenoxy)phenoxy]propanoyl chloride.

To a solution of 2,2-dimethyl-1,3-dioxane-4,4-dione (858 mg., 1.2 eq.) in CH2Cl2 (20 ml.) and pyridine (0.8 ml, 2 eq.) is added slowly at 0°, a solution of the foregoing acid chloride in CH2Cl2 (5 ml.). The resulting mixture is stirred at room temperature for 2 hours. The reaction is then worked up by pouring into water, acidifying with dilute HCl and extracting with CH2Cl2. The extracts are combined, washed with brine, dried and evaporated to give (R)-2-[4-(4-trifluoromethylphenoxy)phenoxy]-propionyl meldrum's acid, an oil (II).

The foregoing meldrums acid is treated with ethanol (20 ml.) at 120° for 4 hours. After aqueous workup, the product is purified by preparative thin layer chromatography on silica gel to give (R) ethyl 4-[4-(4-trifluoromethylphenoxy)phenoxy]-3-oxopentanoate, MS m/e 424(M+).

nmr (CDCl3): δ 8.8(t, 3H, OCH2CH3), 8.5

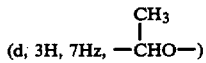

(d, 3H, 7Hz, —CHO—)

6.44

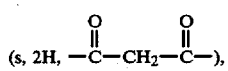

(s, 2H, —C—CH2—C—), 5.82 (q, 2H, OCH2CH3), 5.3

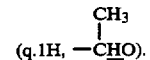

(q.1H, —CHO).

Specific rotation [α]D25 = +10.99 (c = 20 mg/ml in CDCl3).

EXAMPLE 74

The procedure of Example 1 is repeated using each of methanol and n-butanol in place of ethanol to yield:
(R)-methyl 4-[4-(4-trifluoromethylphenoxy)phenoxy]-3-oxopentanoate and
(R)-n-butyl 4-[4-(4-trifluoromethylphenoxy)phenoxy]-3-oxopentanoate.

EXAMPLE 75

The (R) enantiomer prepared in Example 1 was tested at 10 lb/acre on grass weeds (watergrass, greenfoxtail, wild oats and shattercane) and gave 100% control both pre- and past-emergent application. Post-emergent application of the same compound on broadleaf plants (velvet leaf, annual morningglory, mustard and soybeans) gave only 8% injury.

EXAMPLE 76

A mixture of (R)-2-[4-(4-trifluoromethylphenoxy)-phenoxy]propionyl meldrum acid (5 mm.) and benzyl alcohol (20 mm.) is heated at 100° for about 4 hours. After aqueous workup, the product is purified by their layer chronatography on silica gel to give (R)-benzyl4-[4-(4-trifluoromethylphenoxy)phenoxy]-3-oxopentanoate.

The foregoing benzyl ester (4 mm.) is subjected to hydrogenolysis using palladium/charcoal (0.4 mm.) in 20 ml ethanol, one atmosphere, for about 20 minutes. The reaction is worked up by filtering and then concentrating filtrate under reduced pressure to yield (R)-4-[4-(4-trifluoromethylphenoxy)phenoxy]-3-oxopentanoic acid. The sodium salt and potassium salt of the thus-obtained (R) acid are prepared in conventional manner by treatment with base.

What is claimed is:
1. A compound selected from those of the formula B':

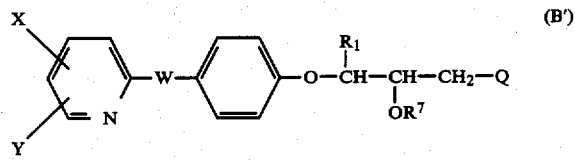

(B')

wherein
W is O, or S;
each of X and Y is independently selected from hydrogen, bromo, chloro, fluoro, lower alkyl, lower alkoxy, lower alkoxycarbonyl, nitro, cyano, trifluoromethyl, chlorodifluoromethyl, fluoromethyl, chloromethyl and difluoromethoxy;
$R^1$ is hydrogen or lower alkyl;
Q is selected from $COOR^3$, $COSR^3$, or $CONR^4R^5$ in which $R^3$ is hydrogen, lower alkyl, lower haloalkyl, lower cyanoalkyl, lower alkenyl, lower haloalkenyl, lower alkynyl, lower alkoxyalkyl, lower dialkylaminoalkyl, lower alkylthioalkyl, lower alkylsulfinylalkyl, lower alkylsulfonylalkyl, tetrahydrofuranylmethyl, tetrahydropyranylmethyl, pyridylmethyl, benzyl, halobenzyl, lower alkylbenzyl, lower alkoxybenzyl, phenyl, halophenyl, lower alkoxyphenyl, lower alkylphenyl, cycloalkyl, cycloalkalkyl, N-alkylideneamino, sodium, potassium, magnesium, or calcium;

each of $R^4$ and $R^5$ is independently selected from hydrogen, lower alkyl, lower hydroxyalkyl, lower alkoxyalkyl, or lower alkylsulfonyl; and $R^7$ is selected from carboxylic acyl, phenylacyl, phenoxyacyl, (X,Y-substituted)phenoxyacyl, (X-substituted)phenylacyl, (X,Y-substituted phenoxy)phenylacyl, and (X,Y-substituted phenoxy)-(X-substituted phenyl)acyl.

2. A compound of the formula

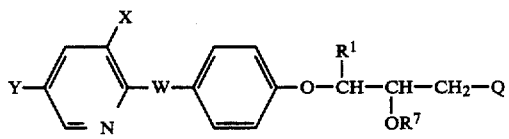

according to claim 1.

3. A compound according to claim 2, wherein W is oxygen, $R^1$ is methyl, Q is

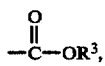

and $R^7$ is carboxylic acyl, phenylacyl, phenoxyacyl, (X,Y-substituted)phenoxyacyl, (X-substituted)phenylacyl, (X,Y-substituted phenoxy)phenylacyl, and (X,Y-substituted phenoxy)-(X-substituted phenyl)acyl.

4. A compound according to claim 3, wherein each of X and Y is independently selected from the group consisting of hydrogen, bromo, chloro, fluoro, trifluoromethyl, and nitro.

5. A compound according to claim 4, wherein $R^3$ is selected from the group consisting of hydrogen, lower alkyl and lower hydroxyalkyl.

6. A compound according to claim 5, wherein $R^7$ is selected from the group consisting of formyl, chloroformyl, acetyl, chloroacetyl, (2,2-dichloro)propionyl, benzoyl, dichlorobenzoyl, nitrobenzoyl, phenoxy nitrobenzoyl and (trifluoromethyl,chloro)phenoxynitrobenzoyl.

7. A compound according to claim 5 of the formula

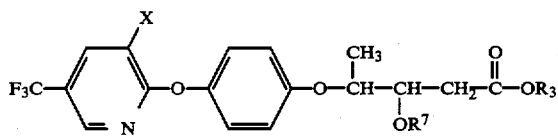

wherein X in the trifluoromethylpyridyl group is hydrogen or chloro and $R^7$ is formyl, acetyl, chloroformyl, chloroacetyl, (2,2-dichloro)propionyl, benzoyl, dichlorophenoxybutanoyl, and (trifluoromethyl,chloro)phenoxynitrobenzoyl.

8. Ethyl 4-[4-(3-chloro, 5-trifluoromethyl-2-pyridyloxy)phenoxy]-3-acetoxypentanoate, according to claim 7.

9. Ethyl 4-[4-(3-chloro, 5-trifluoromethyl-2-pyridyloxy)phenoxy]-3-formoyloxypentanoate, according to claim 7.

10. Methyl 4-[4-(5-trifluoromethyl-2-pyridyloxy)phenoxy]-3-acetoxypentanoate, according to claim 7.

11. A herbicidal composition which comprises a herbicidally effective amount of a compound of claim 1 and a suitable carrier material.

12. A herbicidal composition which comprises a herbicidally effective amount of a compound of claim 2 and a suitable carrier material.

13. A herbicidal composition which comprises a herbicidally effective amount of a compound of claim 3 and a suitable carrier material.

14. A herbicidal composition which comprises a herbicidally effective amount of a compound of claim 4 and a suitable carrier material.

15. A herbicidal composition which comprises a herbicidally effective amount of a compound of claim 5 and a suitable carrier material.

16. A herbicidal composition which comprises a herbicidally effective amount of a compound of claim 6 and a suitable carrier material.

17. A herbicidal composition which comprises a herbicidally effective amount of a compound of claim 7 and a suitable carrier material.

18. A herbicidal composition which comprises a herbicidally effective amount of a compound of claim 8 and a suitable carrier material.

19. A herbicidal composition which comprises a herbicidally effective amount of a compound of claim 9 and a suitable carrier material.

20. A herbicidal composition which comprises a herbicidally effective amount of a compound of claim 10 and a suitable carrier material.

21. A method for the control of weeds which comprises applying to the locus of said weeds a herbicidally effective amount of a compound of claim 1.

22. A method for the control of weeds which comprises applying to the locus of said weeds a herbicidally effective amount of a compound of claim 2.

23. A method for the control of weeds which comprises applying to the locus of said weeds a herbicidally effective amount of a compound of claim 3.

24. A method for the control of weeds which comprises applying to the locus of said weeds a herbicidally effective amount of a compound of claim 4.

25. A method for the control of weeds which comprises applying to the locus of said weeds a herbicidally effective amount of a compound of claim 5.

26. A method for the control of weeds which comprises applying to the locus of said weeds a herbicidally effective amount of a compound of claim 6.

27. A method for the control of weeds which comprises applying to the locus of said weeds a herbicidally effective amount of a compound of claim 7.

28. A method for the control of weeds which comprises applying to the locus of said weeds a herbicidally effective amount of a compound of claim 8.

29. A method for the control of weeds which comprises applying to the locus of said weeds a herbicidally effective amount of a compound of claim 9.

30. A method for the control of weeds which comprises applying to the locus of said weeds a herbicidally effective amount of a compound of claim 10.

* * * * *